United States Patent [19]

Johnson

[11] 4,209,520
[45] Jun. 24, 1980

[54] HEXAHYDRO-1-HYDROXY-9-HYDROX-YMETHYL-3-SUBSTITUTED-6H-DIBEN-ZO[b,d]PYRANS AS ANALGESIC AGENTS

[75] Inventor: Michael R. Johnson, Gales Ferry, Conn.

[73] Assignee: Pfizer Inc., New York, N.Y.

[21] Appl. No.: 952,314

[22] Filed: Oct. 18, 1978

Related U.S. Application Data

[60] Continuation-in-part of Ser. No. 934,319, Aug. 16, 1978, abandoned, which is a division of Ser. No. 807,439, Jun. 17, 1977, Pat. No. 4,133,819.

[51] Int. Cl.$^2$ .................... A61K 31/44; A61K 31/35;
                              C07D 405/12; C07D 311/80
[52] U.S. Cl. ................................ 424/263; 260/345.3;
               260/326.8; 424/283; 424/274; 424/267;
               544/124; 544/149; 546/269; 546/196; 546/194
[58] Field of Search .................... 260/345.3; 546/269;
                                               424/283, 263

[56] References Cited

U.S. PATENT DOCUMENTS

| | | | |
|---|---|---|---|
| 3,507,885 | 4/1970 | Fahrenholtz | 260/345.3 |
| 3,873,576 | 3/1975 | Petrzilka | 260/345.3 |
| 3,901,926 | 8/1975 | Winn | 260/345.3 |
| 3,927,036 | 12/1975 | Lee | 260/345.3 |
| 3,968,125 | 7/1976 | Archer | 260/345.3 |

OTHER PUBLICATIONS

Edery et al., N.Y. Academy of Science, Annals, vol. 191, pp. 40–53, (1971).
Razdan et al., JACS, 95, 2361, (1973).
Mechoulam, Ed., "Marijuana, Chemistry, Pharmacology, Metabolism and Clinical Effects," Academic Press, New York, N.Y., 1973, p. 58.

*Primary Examiner*—Nicky Chan
*Attorney, Agent, or Firm*—Connolly and Hutz

[57] ABSTRACT

Hexahydro-1-hydroxy-9-hydroxymethyl-3-substituted-6H-dibenzo[b,d]pyrans useful as analgesic agents, derivatives thereof, intermediates therefor and processes for their preparation.

14 Claims, No Drawings

HEXAHYDRO-1-HYDROXY-9-HYDROXYMETHYL-3-SUBSTITUTED-6H-DIBENZO[B,D]PYRANS AS ANALGESIC AGENTS

CROSS-REFERENCE TO RELATED APPLICATIONS

This application is a continuation-in-part of application Ser. No. 934,319, filed Aug. 16, 1978, and now abandoned which in turn is a division of application Ser. No. 807,439, filed June 17, 1977 and now U.S. Pat. No. 4,133,819.

BACKGROUND OF THE INVENTION

1. Field of the Invention

This invention relates to certain 6a,7,9,9,10,10a-hexahydro-1-hydroxy-9-hydroxymethyl-3-substituted6H-dibenzo[b,d]pyrans and derivatives thereof useful as CNS agents, especially as analgesics and tranquilizers, in mammals, including man; and to intermediates therefor.

2. Description of the Prior Art

The search for new and improved analgesic agents has, for the past several years, centered upon cannabinol-type compounds. Large numbers of derivatives of such compounds and modification of the basic dibenzo[b,d]pyran ring system common to such compounds have been described in the literature. Several review articles have appeared which contain extensive bibliographies to the synthesis, structure, and biological properties of the naturally-occurring dibenzo[b,d]pyrans as well as to derivatives and modifications therefor. Of particular interest are the following review articles: R. Mechoulam, Ed., "Marijuana. Chemistry, Pharmacology, Metabolism and Clinical Effects", Academic Press, New York, N.Y. 1973; Mechoulam, et al, *Chemical Reviews*, 76, 75–112 (1976). In addition to these review articles from the chemical literature, rather comprehensive reviews appear in U.S. Pat. Nos. 3,886,184 and 3,968,125. However, despite the large numbers of such compounds described in the literature, the search for new and improved agents continues thus pointing to the lack of an agent useful for the control of broad levels of pain and accompanied by a minimum of side-effects.

U.S. Pat. No. 3,968,125, issued July 6, 1976, describes a series of 6a,7,8;9,10,10a-hexahydro-1-hydroxy-3-alkyl-6H-dibenzo[b,d]pyran-9-ols useful as hypotensive agents, as psychotropic drugs, particularly as anti-anxiety and/or antidepressant drugs, and as sedative and/or analgesic drugs.

Mechoulam, Ed., "Marijuana. Chemistry, Pharmacology, Metabolism and Clinical Effects", Academic Press, New York, N.Y., 1973, at page 58, describes 6a,7,8,10a-tetrahydro-1-hydroxy-3-alkyl-6,6-dimethyl-9-hydroxymethyl-6H-dibenzo[b,d]pyran and 6a,7,10,-10a-tetrahydro-1-hydroxy-3-alkyl-6,6-dimethyl-9-hydroxymethyl-6H-dibenzo[b,d]pyran, which are metabolites of the corresponding tetrahydrocannabinols having a methyl group at the 9-position.

Razdan et al., *J. Am. Chem. Soc.*, 95, 2361–2 (1973) describe 7-hydroxyhexahydrocannabinol and a compound "tentatively unidentified" as its $C_1$-epimer.

In addition to the problem of addiction liability, the opiate analgesics have a limited use in the treatment of chronic pain states such as cancer because tolerance to the analgesic activity is developed upon repeated administration of these drugs. While the potent 9-hydroxy-dibenzo[b,d]pyran analgesics represent a therapeutic advance since they are non-narcotic drugs, it has been found that rapid tolerance develops to their analgesic action thereby limiting the use of these agents in chronic pain states where repeated dosing over long periods of time is necessary to provide continued pain relief.

SUMMARY OF THE INVENTION

It has now been found that certain 6a,7,8,9,10,10a-hexahydro-1-hydroxy-9-hydroxymethyl-3-substituted-6H-dibenzo[b,d]-pyrans and derivatives thereof having formula I below are effective as CNS agents, especially as analgesics and tranquilizers, which are non-narcotic and free of addiction liability. In addition, significantly less tolerance is exhibited to the analgesic activity of these compounds than, for example, the compounds wherein the 9-position bears a hydroxy group in place of the hydroxymethyl group, thus making them particularly useful in the treatment of chronic pain. The compounds have formula I below

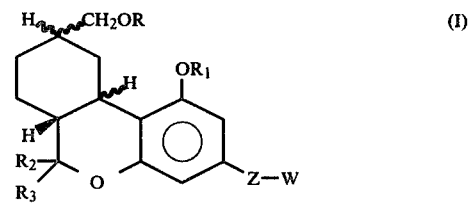

wherein

R is selected from the group consisting of hydrogen and alkanoyl having from one to five carbon atoms;

$R_1$ is selected from the group consisting of hydrogen, alkanoyl having from one to five carbon atoms and —CO—$(CH_2)_p$—$NR_4R_5$ wherein p is 0 or an integer from 1 to 4; each of $R_4$ and $R_5$ when taken individually is selected from the group consisting of hydrogen and alkyl having from one to four carbon atoms; $R_4$ and $R_5$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

each of $R_2$ and $R_3$ is selected from the group consisting of hydrogen and methyl;

Z is selected from the group consisting of
(a) alkylene having from one to ten carbon atoms;
(b) —$(alk_1)_m$—O—$(alk_2)_n$— wherein each of $(alk_1)$ and $(alk_2)$ is alkylene having from one to ten carbon atoms, with the proviso that the summation of carbon atoms in $(alk_1)$ plus $(alk_2)$ is not greater than ten; each of m and n is 0 or 1; and W is selected from the group consisting of hydrogen, pyridyl and

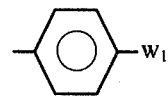

wherein $W_1$ is selected from the group consisting of hydrogen, fluoro and chloro; with the proviso that when W is hydrogen, Z is —$(alk_1)_m$—O—$(alk_2)_n$—;

and the pharmaceutically acceptable acid addition salts of those compounds wherein $R_1$ is CO—$(CH_2)_p$—$NR_4R_5$ and/or W is pyridyl.

Also included in this invention are various derivatives of said compounds which are useful as dosage forms and intermediates therefor. Among such derivatives are the pharmaceutically acceptable acid addition salts of compounds of formula I. Representative of such salts are mineral acid salts such as the hydrochloride, hydrobromide, sulfate, nitrate, phosphate; organic acid salts such as the citrate, acetate, sulfosalicylate, tartrate, glycolate, malonate, maleate, fumarate, malate, 2-hydroxy-3-naphthoate, pamoate, salicylate, stearate, phthalate, succinate, gluconate, mandelate, lactate and methanesulfonate.

Compounds having formula I contain asymmetric centers at the 6a- and/or 10a-positions. There may be additional asymmetric centers in the 3-position substituent (—Z—W), and 5-, 6- and 9-positions. Diastereomers with the 9β-configuration are generally favored over the 9α-isomers because of greater (quantitatively) biological activity. For the same reason, the trans-(6a,10a)-diastereomers are generally favored over the cis-(6a,10a)-diastereomers. Among the enantiomers of a given compound, one will generally be favored over the other and the racemate because of its greater activity. The enantiomer favored is determined by the procedures described herein. For convenience, the above formula depicts the racemic compounds. However, the above formula is considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers, is determined by the biological evaluations described below.

Further, various intermediates useful in the preparation of compounds having formula I are also included in this invention. The intermediates have the formula:

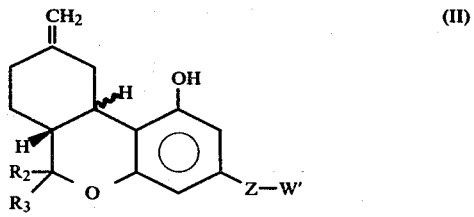

(II)

wherein $R_2$, $R_3$ and Z are as described above and W' is selected from the group consisting of pyridyl and

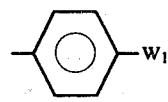

wherein $W_1$ is selected from the group consisting of hydrogen, fluoro and chloro; with the proviso that when W is hydrogen, Z is —$(alk_1)_m$—O—$(alk_2)_n$—; and the pharmaceutically acceptable acid addition salts of those compounds wherein $R_1$ is —CO—$(CH_2)_p$—$NR_4R_5$ and/or W is pyridyl.

Asymmetric centers may exist in compounds of formula II at all positions previously noted with respect to formula I except, of course, at the 9-position.

The favored compounds of this invention are those wherein the hydroxymethyl group at the 9-position has the β-configuration. Such compounds are of greater potency and efficacy than are the corresponding α-compounds. Of special interest are compounds of formula I wherein the several variables have the significance shown below in Table A:

TABLE A

| R | $R_1$ | $R_2$ | $R_3$ | Z | m | n | W |
|---|---|---|---|---|---|---|---|
| H, COCH$_3$ | H, COCH$_3$ | H, CH$_3$ | H, CH$_3$ | alkylene having 4 to 6 carbon atoms | — | — | C$_6$H$_5$ pyridyl |
| H, COCH$_3$ | H, COCH$_3$ | H, CH$_3$ | H, CH$_3$ | $(alk_1)_m$—O—$(alk_2)_n$ | 0 | 1 | H, C$_6$H$_5$ |

Particularly favored because of their greater potency are those compounds of formula I, Table A, wherein the variables have the significance shown in Table B below:

TABLE B

| R | $R_1$ | $R_2$ | $R_3$ | Z | m | n | W |
|---|---|---|---|---|---|---|---|
| H | H | CH$_3$ | CH$_3$ | CH(CH$_3$)(CH$_2$)$_3$ | — | — | C$_6$H$_5$ |
| H | H | CH$_3$ | CH$_3$ | —O—CH(CH$_3$)(CH$_2$)$_3$ | 0 | 1 | C$_6$H$_5$ |
| H | H | CH$_3$ | CH$_3$ | —O—CH(CH$_3$)(CH$_2$)$_6$ | 0 | 1 | H |
| H | H | H | CH$_3$ | —O—CH(CH$_3$)(CH$_2$)$_3$ | 0 | 1 | C$_6$H$_5$ |

DETAILED DESCRIPTION OF THE INVENTION

The compounds of this invention are readily prepared from the corresponding 9-oxo compunds having formula III below:

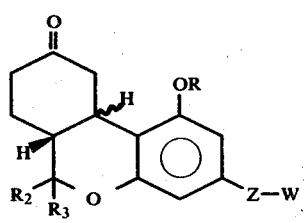

(III)

wherein R, $R_2$, $R_3$, Z and W are as defined above via the Wittig reaction with methylene triphenylphosphorane or other appropriate methylide. The usual procedure comprises generating the Wittig reagent; that is, the methylide, in situ and, immediately following generation of the methylide, reacting it with the appropriate 9-ozo compound. A convenient procedure for generating the methylide comprises reacting sodium hydride with dimethyl sulfoxide at a temperature of from about 50° C.-80° C., usually until evolution of hydrogen ceases, followed by reacting the resulting solution of methyl sulfinyl carbanion with, for example, methyl triphenyl phosphonium bromide at a temperature of from about 10° C. to about 80° C. To the thus-produced solution of the ylide is then added the appropriate 9-oxo compound and the mixture stirred at temperatures ranging from about room temperature to 80° C. The 9-methylene compound thus produced is isolated by known procedures. Fahrenholtz, U.S. Pat. No. 3,636,058, reports the preparation of several 6a,7,8,9,10,10a-hexahydro-1-hydroxy-3-alkyl-6,6-dimethyl-9-methylene-6H-dibenzo[b,d]pyrans.

Other methods of generating the methylide are, of course, known and can be used in lieu of the above-described procedure. Typical procedures are described by Maercker, *Organic Reactions*, 14, 270 (1965).

In compounds having formula III, the hydroxy group at the 1-position can be protected if desired as, for example, by conversion to an alkanoyloxy derivative. Other protecting groups can, of course, be used. The hydroxyl group can be converted to ethers such as, for example, tetrahydropyranyl ethers. However, protection of the hydroxy group is not absolutely necessary if sufficient base is present to convert the hydroxy group to an alkoxide.

The 9-methylene compounds are then converted to corresponding hydroxymethyl derivatives by hydroboration-oxidation. A convenient procedure and one favored for the hydroboration step comprises reacting the 9-methylene compound with borane in tetrahydrofuran at temperatures from about $-10°$ C. to about room temperature. The temperature is not critical. However, temperatures within the range indicated above produce satisfactory yields. The reaction is generally conducted in tetrahydrofuran or diethylene glycol dimethyl ether (diglyme). The borane is conveniently used as the borane-tetrahydrofuran complex because of its availability and stability. The borane product is not isolated but is directly oxidized to the desired hydroxymethyl compound. A typical procedure comprises decomposing the excess borane by addition of water and then adding a suitable base such as sodium acetate, and usually a small excess of hydrogen peroxide. The oxidation is conducted at temperatures from about $-10°$ to about $-50°$ C. and the product recovered by known procedures.

In the Wittig reaction, as noted above, the 1-hydroxy group can be protected by appropriate means as by formation of an alkanoyl derivative thereof. The Wittig reaction results in removal of this protecting group to regenerate the 1-hydroxy group. It is not necessary to re-protect the 1-hydroxy group for the subsequent hydroboration-oxidation procedure.

The necessary 6a,7,10,10a-tetrahydro-1-hydroxy-6,6-$R_2R_3$-3-substituted-6H-dibenzo[b,d]pyran-9(8H)-ones are known compounds described in Dutch specification No. 7612174, in U.S. Pat. No. 3,968,125 and by R. Mechoulam, Ed., "Marijuana. Chemistry, Pharmacology, Metabolism and Clinical Effects", Academic Press, New York, N.Y. (1973), pages 45, 46 and 56.

Esters of compounds of formula I wherein $R_1$ is alkanoyl or $-CO-(CH_2)_p-NR_4R_5$ are readily prepared by reacting formula I compounds with the appropriate alkanoic acid or acid of formula $HOOC-(CH_2)_p-NR_4R_5$ in the presence of a condensing agent such as dicyclohexylcarbodiimide. Alternatively, they are prepared by reaction of a formula I compound with the appropriate alkanoic acid chloride or anhydride, e.g., acetyl chloride or acetic anhydride, in the presence of a base such as pyridine.

Esters in which each of the R and $R_1$ groups is esterified are prepared by acylation according to the above-described procedures. Compounds in which only the 9-hydroxymethyl group is acylated are obtained by mild hydrolysis of the corresponding diacyl derivative, advantage being taken of the greater ease of hydrolysis of the phenolic acyl group. The thus-produced formula I compounds bearing 1-hydroxy-9-acyl substitution can then be acylated further with a different acylating agent to produce a diesterified compound in which the ester group at the 1- and the 9-positions are different.

The presence of a basic group in the ester moiety ($OR_1$) of the compounds of this invention permits formation of acid-addition salts involving said basic group. When the herein described basic esters are prepared via condensation of the appropriate amino acid hydrochloride (or other acid addition salt) with the appropriate compound of formula I in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with formula I compounds wherein —Z—W contains a basic group. Such salts are prepared by standard procedures. The basic ester derivatives are, of course, able to form mono- or di-acid addition salts because of their dibasic functionality.

The analgesic properties of the compounds of this invention are determined by tests using nociceptive stimuli.

Tests Using Thermal Nociceptive Stimuli (a) Mouse Hot Plate Analgesic Testing The method used is modified after Woolfe and MacDonald, *J. Pharmacol. Exp. Ther.*, 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50} = 4–5.6$ mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., *Arch. int. Pharmacodyn.*, 122, 434 (1959). Male albino mice (19–21 g.)

of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trail is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch Med. Wschr.*, 55, 731-732 (1929) is used to ascertain the effects of the test compound on aggressive attacking responses elicited by a stimulus pinching the tail. Male albino rats (50-60 g.) of the Charles River (Sprague-Dawley) CD strain are used. Prior to drug treatment, and again at 0.5, 1, 2, and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278-285 (1968) is used for determining pain thresholds. Male albino rats (175-200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \ MPE = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

EXAMPLE 1 dl-6aβ,7,10,10aα-Tetrahydro-1-acetoxy-6,6-dimethyl-3-[2-(5-phenylpentyloxy)]-6H-dibenzo[b,d]pyran-9(8H)-one To a solution of dl-6aβ,7,10,10aα-tetrahydro-1-hydroxy-6,6-dimethyl-3-[2-(5-phenylpentyloxy)]-6H-dibenzo[b,d]pyran-9(8H)-one (4.06 gm., 10 mmoles) dissolved at 0° C. in 15 ml. pyridine is added 15 ml. (excess) acetic anhydride and the resultant solution is stirred at ice temperatures for 30 minutes. The mixture is poured onto ice/water (100 ml.), neutralized with dilute HCl and extracted with ethyl acetate (2×100 ml.). The pooled organic layers are washed with water (1×50 ml.), brine (1×50 ml.), dried over MgSO₄, filtered and evaporated under reduced pressure. Crystals are obtained from ether/pentane (1:1) to afford 3.43 gm. (76%) of the title compound, m.p. 95.5°–97° C.

TLC system: pentane/ether (1:1) $R_f$ 0.2.

IR (KBr) 2.95μ (W), 3.40 (M), 5.62 (S), 5.72 (S), 6.12 (S), 6.31 (S), 6.70 (S).

Analysis: Calc'd for $C_{28}H_{34}O_5$: C, 74.64; H, 7.61%. Found: C, 74.55; H, 7.59%.

$^1$H NMR (60 MHz) $\delta_{CDCl_3}^{TMS}$ (ppm): 7.22 (s, 5H), 6.26 (d, 1H), 6.18 (d, 1H), 4.0–4.5 (m, 1H), 2.22 (s, 3H), 1.48 (s, 3H), 1.22 (d, 3H), 1.04 (s, 3H), 3.0–3.55 (m, 2H), 2.40–2.80 (m, 2H), 1.42–2.20 (m, 4H).

EXAMPLE 2 dl-6aβ,7,8,9,10,10aα-Hexahydro-1-hydroxy-6,6-dimethyl-9-methylene-3-[2-(5-phenylpentyloxy)]-6H-dibenzo[b,d]pyran To 50% sodium hydride/mineral oil (1.52 gm., 32 mmoles), (washed 3×25 ml. portions of pentane) is added 60 ml. of dry dimethylsulfoxide and the mixture heated at 50° C. for 2.5 hours. The heterogeneous mixture turns homogeneous during this heating period. 11.86 (34 mmoles) of methyl triphenylphosphonium bromide is then added in one portion. The yellow solution is heated at 63°–65° C. for 2.5 hours and 1.89 g. (4.2 mmoles) of dl-6aβ,7,10,10aα-tetrahydro-1-acetoxy-6,6-dimethyl-3-[2-(5-phenylpentyloxy)]-6H-dibenzo[b,d]-pyran-9(8H)-one dissolved in 60 ml. of dimethylsulfoxide is added all at once and heated at 63°–65° C. for an additional 1.5 hours. The reaction is then poured onto 150 ml. ice water/25 g. NaHCO$_3$ and extracted 2×50 ml. with ether. The combined ether extracts are dried over MgSO$_4$, decolorized with charcoal and filtered through a bed of silica gel to afford a colorless oil which is chromatographed on 50 g. silica gel (eluting solvent cyclohexane). A non-polar impurity is eluted first, then the polarity of the solvent is increased to ether/cyclohexane (1:10) thus affording 1.099 gm. (64.1%) of the title product as a colorless oil.

IR (smear) 2.80μ (w), 3.00 (w), 3.40 (s), 3.48 (s), 6.17 (s), 6.27 (s).

Mass Spec. M+ 406 (100%), 391 (12%), 260 (40%), 244 (40%).

TLC: Brinkman Plate Benzene/Ether (1:1) $R_f$ 0.9.

$^1$H NMR (60 MHz) $\delta_{CDCl_3}^{TMS}$ (ppm): 7.18 (s, 5H), 5.98 (d, 1H), 5.79 (d, 1H), 5.67 (s, 1H), 3.9–4.4 (m, 1H), 3.5–4.9 (m, 4H), 1.38 (s, 3H, CHCl$_3$), 1.2 (d, 3H), 1.05 (s, 3H).

EXAMPLE 3 dl-6aβ,7,8,9,10,10aα-Hexahydro-1-hydroxy-6,6-dimethyl-9β-hydroxymethyl-3-[2-(5-phenylpentyloxy]-6H-dibenzo[b,d]pyran A solution of 0.849 g. dl-6aβ,7,8,10,10aα-pentahydro-1-hydroxy-6,6-dimethyl-9-methylene-3-[2-(5-phenylpentyloxy)]-6H-dibenzo[b,d]pyran (2 mmoles) dissolved in 20 ml. of dry tetrahydrofuran is cooled to 0° C. in an ice/water bath. Borane-tetrahydrofuran complex (3.0 ml., 3 mmoles, 1 M solution) is added and the colorless solution allowed to stir overnight at ambient temperature (18 hours). The mixture is cooled in ice and 5 ml. of water added to decompose the excess reagent. It is stirred for 15 minutes and then 2 ml. (6 mmoles) of 3 N sodium acetate followed by 2 ml. 30% hydrogen peroxide added. It is stirred at 0° C. for 15 minutes then allowed to warm to room temperature and stirred overnight (24 hours). The reaction mixture is poured onto 100 ml. ice/water and then extracted with 2×50 ml. ether. The combined ether extracts are washed with sodium sulfite until negative to starch KI test, dried over MgSO$_4$ and evaporated to dryness to yield a pale yellow oil which is chromatographed on 35 g. Brinkman silica gel (eluting solvent cyclohexane/ether 3:1) to afford a colorless foam weighing 364 mg. (43%).

IR (KBr) 2.95μ (s), 3.40 (s), 6.17 (s), 6.30 (s).

Mass Spec. 424 (100%), 278 (79%), 279 (41%), 236 (29%).

Analysis: Calc'd for $C_{27}H_{36}O_4$: C, 76.38; H, 8.55%. Found: C, 75.73; H, 8.77%.

EXAMPLE 4 dl-6aβ-7,8,9,10,10aα-Hexahydro-1-hydroxy-9β-acetoxymethyl-6,6-dimethyl-3-[2-(5-phenylpentyloxy)]-6H-dibenzo[b,d]pyran A solution of 0.1 mole of dl-6aβ,7,8,9,10,10aα-hexahydro-1-hydroxy-6,6-dimethyl-9β-hydroxymethyl-3-[2-(5-phenylpentyloxy)]-6H-dibenzo[b,d]pyran in 100 ml. of acetonitrile is treated with 0.1 mole of acetic anhydride and the mixture heated for 12 hours under nitrogen. It is then poured onto ice/water and extracted with ethyl acetate (2×100 ml.), the extracts combined, washed with brine and dried (MgSO$_4$). Evaporation under reduced pressure followed by silica gel chromatography affords the title product as an oil.

Similarly, substitution of anhydrides of propionic, butyric and valeric acid for acetic anhydride affords the corresponding ester derivatives.

EXAMPLE 5

The following compounds are similarly prepared according to the procedures of Examples 1–3 but using the appropriate 9-oxo compound as reactant.

| $CH_2$—OH | $R_2$ | $R_3$ | 6a, 10a | Z | W |
|---|---|---|---|---|---|
| β | $CH_3$ | $CH_3$ | trans | $CH(CH_3)(CH_2)_3$ | $C_6H_5$ |
| β | $CH_3$ | $CH_3$ | cis | $CH(CH_3)(CH_2)_3$ | $C_6H_5$ |

-continued

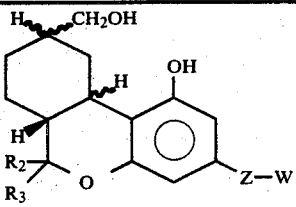

| CH$_2$—OH | R$_2$ | R$_3$ | 6a, 10a | Z | W |
|---|---|---|---|---|---|
| β | CH$_3$ | CH$_3$ | trans | CH(CH$_3$)(CH$_2$)$_4$ | C$_6$H$_5$ |
| β | CH$_3$ | CH$_3$ | cis | CH(CH$_3$)(CH$_2$)$_4$ | C$_6$H$_5$ |
| β | CH$_3$ | CH$_3$ | trans | CH$_2$CH$_2$ | C$_6$H$_5$ |
| β | CH$_3$ | CH$_3$ | trans | CH(CH$_3$)(CH$_2$)$_2$ | C$_6$H$_5$ |
| β | CH$_3$ | CH$_3$ | cis | CH(CH$_3$)(CH$_2$)$_2$ | C$_6$H$_5$ |
| β | CH$_3$ | CH$_3$ | trans | CH(CH$_3$)(CH$_2$)$_3$—O— | C$_6$H$_5$ |
| β | CH$_3$ | CH$_3$ | trans | CH(CH$_3$)(CH$_2$)$_3$ | 4-pyridyl |
| β | CH$_3$ | CH$_3$ | trans | CH(CH$_3$)CH$_2$—O—(CH$_2$)$_2$ | C$_6$H$_5$ |
| β | CH$_3$ | CH$_3$ | cis | CH(CH$_3$)CH$_2$—O—(CH$_2$)$_2$ | C$_6$H$_5$ |
| β | CH$_3$ | CH$_3$ | trans | O—CH(CH$_3$)(CH$_2$)$_5$ | H |
| β | CH$_3$ | CH$_3$ | cis | O—CH(CH$_3$)(CH$_2$)$_5$ | H |
| β | CH$_3$ | CH$_3$ | trans | O—CH(CH$_3$)(CH$_2$)$_3$ | C$_6$H$_5$ |
| β | CH$_3$ | CH$_3$ | cis | O—CH(CH$_3$)(CH$_2$)$_3$ | C$_6$H$_5$ |
| β | CH$_3$ | CH$_3$ | trans | O—CH(CH$_3$)(CH$_2$)$_2$ | C$_6$H$_5$ |
| β | CH$_3$ | CH$_3$ | cis | O—CH(CH$_3$)(CH$_2$)$_2$ | C$_6$H$_5$ |
| β | CH$_3$ | CH$_3$ | trans | O— | C$_6$H$_5$ |
| β | CH$_3$ | CH$_3$ | trans | (CH$_2$)$_5$ | H |
| β | CH$_3$ | CH$_3$ | cis | (CH$_2$)$_5$ | H |
| β | CH$_3$ | CH$_3$ | trans | CH(CH$_3$)(CH$_2$)$_2$—O— | C$_6$H$_5$ |
| β | H | CH$_3$ | trans | CH(CH$_3$)(CH$_2$)$_3$ | C$_6$H$_5$ |
| β | CH$_3$ | CH$_3$ | trans | CH(CH$_3$)CH(CH$_3$)(CH$_2$)$_5$ | H |
| β | H | CH$_3$ | trans | (CH$_2$)$_7$ | C$_6$H$_5$ |
| β | H | CH$_3$ | trans | CH(CH$_3$)CH$_2$ | 2-pyridyl |
| β | CH$_3$ | CH$_3$ | trans | (CH$_2$)$_3$ | 3-pyridyl |
| β | H | H | trans | (CH$_2$)$_2$ | 4-pyridyl |
| β | CH$_3$ | CH$_3$ | trans | C(CH$_3$)$_2$CH$_2$ | H |
| β | CH$_3$ | H | trans | CH(CH$_3$)(CH$_2$)$_2$ | 4-FC$_6$H$_4$ |
| β | CH$_3$ | H | trans | CH(CH$_3$)(CH$_2$)$_2$ | 4-ClC$_6$H$_4$ |
| β | CH$_3$ | CH$_3$ | trans | —O— | C$_6$H$_5$ |
| β | CH$_3$ | CH$_3$ | cis | —O— | 4-FC$_6$H$_4$ |
| β | CH$_3$ | H | trans | —OCH(CH$_3$)(CH$_2$)$_6$ | H |
| β | CH$_3$ | CH$_3$ | trans | —O— | 4-ClC$_6$H$_4$ |
| β | CH$_3$ | CH$_3$ | trans | —O— | 2-pyridyl |
| β | CH$_3$ | CH$_3$ | trans | —O— | 4-pyridyl |
| β | H | H | trans | —OCH(CH$_3$)(CH$_2$)$_3$ | 2-pyridyl |
| β | CH$_3$ | CH$_3$ | trans | C(CH$_3$)$_2$(CH$_2$)$_6$ | H |
| β | CH$_3$ | CH$_3$ | cis | C(CH$_3$)$_2$(CH$_2$)$_6$ | H |
| α | CH$_3$ | CH$_3$ | trans | CH(CH$_3$)(CH$_2$)$_3$ | C$_6$H$_5$ |
| α | CH$_3$ | CH$_3$ | cis | CH(CH$_3$)(CH$_2$)$_4$ | C$_6$H$_5$ |
| α | CH$_3$ | CH$_3$ | trans | OCH(CH$_3$)(CH$_2$)$_5$ | H |
| β | CH$_3$ | CH$_3$ | trans | CH$_2$ | H |
| β | H | CH$_3$ | trans | CH(CH$_3$)(CH$_2$)$_9$ | H |
| β | CH$_3$ | CH$_3$ | trans | (CH$_2$)$_{10}$ | H |
| β | CH$_3$ | CH$_3$ | trans | CH(CH$_3$)(CH$_2$)$_2$O | C$_6$H$_5$ |
| β | CH$_3$ | CH$_3$ | trans | CH$_2$CH(CH$_3$)OCH(CH$_3$)CH$_2$ | C$_6$H$_5$ |
| β | CH$_3$ | CH$_3$ | cis | (CH$_2$)$_3$OCH$_2$ | H |
| β | CH$_3$ | CH$_3$ | trans | (CH$_2$)$_3$O(CH$_2$)$_3$ | H |
| β | CH$_3$ | CH$_3$ | trans | CH(CH$_3$)(CH$_2$)$_2$O(CH$_2$)$_4$ | C$_6$H$_5$ |
| β | CH$_3$ | CH$_3$ | trans | (CH$_2$)$_4$O(CH$_2$)$_5$ | 4-ClC$_6$H$_4$ |
| β | CH$_3$ | CH$_3$ | trans | OCH(CH$_3$)(CH$_2$)$_6$ | H |

The above compounds are converted to their diester derivatives by the procedure of Example 4.

EXAMPLE 6 dl-6aβ,7,8,9,10,10aα-Hexahydro-1-acetoxy-6,6-dimethyl-9β-acetoxymethyl-3-[2-(5-phenylpentyloxy]-6H-dibenzo[b,d]pyran A mixture of 1.0 g. of dl-6aβ,7,8,9,10,10aα-hexahydro-1-hydroxy-6,6-dimethyl-9β-hydroxymethyl-3-[2-(5-phenylpentyloxy]-6H-dibenzo[b,d]pyran and a 5-fold excess of acetic anhydride and pyridine is stirred overnight at room temperature. It is then poured into ice water, the aqueous mixture extracted with ether (3×100 ml.) and the combined extracts washed with water, brine, then dried (MgSO$_4$) and evaporated. The residue is subjected to column chromatography on silica gel, benzene/ether [9:1] as eluting solvent, to give the title product.

Similarly, replacement of acetic anhydride with the anhydrides of propionic, butyric and valeric acids affords the corresponding diesters as their HCl salts.

EXAMPLE 7 dl-6aβ,7,8,9,10,10aα-Hexahydro-1-(4-morpholinobutyryloxy)-6,6-dimethyl-9β-hydroxymethyl-3-[2-(5-phenylpentyloxy)]-6H-dibenzo[b,d]pyran hydrochloride Dicyclohexylcarbodiimide (0.227 g., 1.1 mmole) and 4-N-piperidylbutyric acid hydrochloride (0.222 g., 1.0 mmole) are added to a solution of dl-6aβ,7,8,9,10,10aα-hexahydro-1-hydroxy-6,6-dimethyl-9β-hydroxymethyl-3-[2-(5-phenylpentyloxy)]-6H-dibenzo[b,d]pyran (0.424 g., 1.0 mmole) in methylene chloride (25 ml.) at room temperature. The mixture is stirred for 18 hours and is then cooled to 0° C. and filtered. Evaporation of the filtrate affords the title product.

Similarly, the reactant of this example and the compounds of Example 5 are converted to the basic esters of the hydroxy group at the 1-position by reaction with the appropriate basic acid reactant. Esters wherein the $R_1$ moiety has the following values are thus prepared as their hydrochloride salts:
—CON(CH$_3$)$_2$
—COCH$_2$NH$_2$
—CO(CH$_2$)$_2$N(C$_4$H$_9$)$_2$
—CO(CH$_2$)$_2$—N-(methyl)piperazino
—COC(CH$_3$)$_2$(CH$_2$)$_2$-piperidino
—CO(CH$_2$)$_3$N(C$_2$H$_5$)$_2$
—COCH(CH$_3$)(CH$_2$)$_2$-morpholino
—CO(CH$_2$)$_3$-pyrrolo
—CO(CH$_2$)$_3$-pyrrolidino
—COCH$_2$-pyrrolo
—CO-morpholino
—CO-piperidino
—CO(CH$_2$)$_4$NH$_2$
—CON(C$_4$H$_9$)$_2$
—CO(CH$_2$)$_3$NH(C$_3$H$_7$)
—CO(CH$_2$)$_2$—N-butylpiperazino Careful neutralization with sodium hydroxide affords the free basic esters.

EXAMPLE 8 dl-6aβ,7,8,9,10,10aα-Hexahydro-1-(4-morpholinobutyryloxy)-9β-acetoxymethyl-6,6-dimethyl-3-[2-(5-phenylpentyloxy)]-6H-dibenzo[b,d]pyran A solution of 2.0 g. of the product of Example 7, dl-6aβ,7,8,9,10,10aα-hexahydro-1-(4-morpholinobutyryloxy)-6,6-dimethyl-9β-hydroxymethyl-3-[2-(5-phenylpentyloxy)]-6H-dibenzo[b,d]pyran, in 10 ml. of pyridine is treated at 10° C. with 20 ml. acetic anhydride and the mixture stirred for 18 hours under nitrogen. It is then poured onto ice/water. The mixture is extracted with ethyl acetate (2×100 ml.), the extracts combined, washed with water, brine and dried (MgSO$_4$). Evaporation under reduced pressure affords the title product as an oil.

Similarly, the remaining basic esters of Example 7 are converted to mixed esters. Substitution of anhydrides of propionic, butyric and valeric acid for acetic anhydride affords the corresponding ester derivatives.

EXAMPLE 9 dl-6aβ,7,8,9,10,10aα-Hexahydro-1-acetoxy-9β-hydroxymethyl-6,6-dimethyl-3-[2-(5-phenylpentyloxy)]-6H-dibenzo[b,d]pyran A solution of 0.1 mole of dl-6aβ,7,8,9,10,10aα-hexahydro-1-hydroxy-6,6-dimethyl-9β-hydroxymethyl-3-[2-(5-phenylpentyloxy)]-6H-dibenzo[b,d]pyran in 100 ml. of acetonitrile is treated with 0.1 mole of acetyl-1,5,5-trimethylhydantoin and then heated at 80° C. for 12 hours under nitrogen. Removal of the solvent under reduced pressure and washing with water affords the title product as an oil.

Similarly, the 1-alkanoyloxy derivative of the compounds of this invention are prepared by substitution of the appropriate formula I compound (R=R$_1$=H) in this procedure and by use of the appropriate alkanoyl-1,5,5-trimethylhydantoin acylating agent. (Alkanoyl=-propionyl, butyryl and valeryl).

The alkanoyl 1,5,5-trimethylhydantoins are prepared according to the procedure of Orazi et al., *J. Am. Chem. Soc.*, 91, 2162 (1969).

EXAMPLE 10

General Hydrochloride Salt Formation

Excess hydrogen chloride is added to a solution of the appropriate compound of formula I wherein W is pyridyl and/or R$_1$ is a basic ester group and the resulting precipitate separated and recrystallized from an appropriate solvent, e.g. methanol-ether (1:10).

The remaining compounds of formula I which have a basic group are converted to their hydrochlorides in like manner.

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts are prepared.

EXAMPLE 11

One hundred mg. of dl-6aβ,7,8,9,10,10aα-hexahydro-1-hydroxy-6,6-dimethyl-9β-hydroxymethyl-3-[2-(5-phenylpentyloxy)]-6H-dibenzo[b,d]pyran are intimately mixed and ground with 900 mg. of starch. The mixture is then loaded into telescoping gelatin capsules such that each capsule contains 10 mg. of drug and 90 mg. of starch.

EXAMPLE 12

A tablet base is prepared by blending the ingredients listed below:
Sucrose: 80.3 parts
Tapioca starch: 13.2 parts
Magnesium stearate: 6.5 parts
Sufficient dl-6aβ,7,8,9,10,10aα-hexahydro-1-hydroxy-6,6-dimethyl-9β-hydroxymethyl-3-[2-(5-phenylpentyloxy)]-6H-dibenzo[b,d]pyran is blended into this base to provide tablets containing 0.1, 0.5, 1, 5, 10 and 25 mg. of drug.

EXAMPLE 13

Suspensions of dl-6aβ,7,8,9,10,10aα-hexahydro-1-hydroxy-9β-acetoxymethyl-6,6-dimethyl-3-[2-(5-phenylpentyloxy)]-6H-dibenzo[b,d]pyran are prepared by adding sufficient amounts of drug to 0.5% methylcellulose to provide suspensions having 0.05, 0.1, 0.5, 1, 5 and 10 mg. of drug per ml.

What is claimed is:
1. A compound having the formula

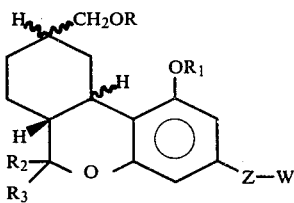

wherein
R is selected from the group consisting of hydrogen and alkanoyl having from one to five carbon atoms;
$R_1$ is selected from the group consisting of hydrogen and alkanoyl having from one to five carbon atoms;
each of $R_2$ and $R_3$ is selected from the group consisting of hydrogen and methyl;
Z is selected from the group consisting of
(a) alkylene having from one to ten carbon atoms;
(b) $—(alk_1)_m—O—(alk_2)_n—$ wherein each of $(alk_1)$ and $(alk_2)$ is alkylene having from one to ten carbon atoms, with the proviso that the summation of carbon atoms in $(alk_1)$ plus $(alk_2)$ is not greater than ten; each of m and n is 0 or 1; and
W is selected from the group consisting of hydrogen and pyridyl;
with the proviso that when W is hydrogen, Z is $—(alk_1)_m—O—(alk_2)_n—$;
and the pharmaceutically-acceptable acid addition salts of those compounds wherein W is pyridyl.

2. A compound according to claim 1 wherein each of R and $R_1$ is hydrogen.

3. A compound according to claim 2 wherein $R_3$ is methyl; Z is alkylene and W is pyridyl.

4. A compound according to claim 3 wherein each of $R_2$ and $R_3$ is methyl; Z is alkylene having from 4 to 6 carbon atoms, and W is 4-pyridyl.

5. The trans (6a,10a) diastereomer compound according to claim 4 wherein Z is $—CH(CH_3)(CH_2)_3—$ and $—CH_2OR$ has the $\beta$-configuration.

6. A compound according to claim 2 wherein $R_3$ is methyl; Z is $—(alk_1)_m—O—(alk_2)_n—$ and W is hydrogen.

7. A compound according to claim 6 wherein each of $R_2$ and $R_3$ is methyl; Z is $—O—(alk_2)—$.

8. The trans (6a,10a) diastereomer compound according to claim 7 wherein Z is $—O—CH(CH_3)(CH_2)_3—$ and $—CH_2OR$ has the $\beta$-configuration.

9. A compound according to claim 1 wherein each of R and $R_1$ is alkanoyl.

10. A compound according to claim 9 wherein $R_3$ is methyl; Z is $—(alk_1)_m—O—(alk_2)_n—$, W is hydrogen and each of R and $R_1$ is acetyl.

11. A compound according to claim 10 wherein Z is $—O—(alk_2)—$ and $R_2$ is methyl.

12. The cis (6a,10a) diastereomer compound according to claim 11 wherein Z is $—OCH(CH_3)(CH_2)_6—$.

13. A process for producing analgesia in a mammal which comprises administering to the mammal an analgesia producing quantity of a compound selected from the group consisting of those having the formula

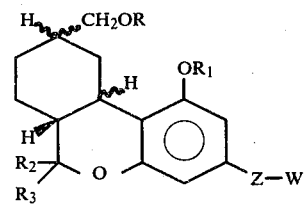

wherein
R is selected from the group consisting of hydrogen and alkanoyl having from one to five carbon atoms;
$R_1$ is selected from the group consisting of hydrogen and alkanoyl having from one to five carbon atoms;
each of $R_2$ and $R_3$ is selected from the group consisting of hydrogen and methyl;
Z is selected from the group consisting of
(a) alkylene having from one to ten carbon atoms;
(b) $—(alk_1)_m—O—(alk_2)_n—$ wherein each of $(alk_1)$ and $(alk_2)$ is alkylene having from one to ten carbon atoms, with the proviso that the summation of carbon atoms in $(alk_1)$ plus $(alk_2)$ is not greater than ten; each of m and n is 0 or 1; and
W is selected from the group consisting of hydrogen and pyridyl and; with the proviso that when W is hydrogen, Z is $—(alk_1)_m—O—(alk_2)_n—$;
and the pharmaceutically acceptable acid addition salts of those compounds wherein W is pyridyl.

14. A composition suitable for producing analgesia in a mammal which comprises a pharmaceutically acceptable carrier and an analgesia producing quantity of a compound of claim 1.

* * * * *

UNITED STATES PATENT AND TRADEMARK OFFICE
CERTIFICATE OF CORRECTION

PATENT NO. : 4,209,520
DATED : June 24, 1980
INVENTOR(S) : Michael R. Johnson

It is certified that error appears in the above–identified patent and that said Letters Patent are hereby corrected as shown below:

Col. 4, lines 2 - 3, delete "with the proviso that when W is hydrogen, Z is $-(alk_1)_m-O-(alk_2)_n-$;".

Signed and Sealed this

Twenty-first Day of October 1980

[SEAL]

Attest:

SIDNEY A. DIAMOND

*Attesting Officer*   *Commissioner of Patents and Trademarks*